(12) United States Patent
Burkinshaw et al.

(10) Patent No.: US 6,277,121 B1
(45) Date of Patent: Aug. 21, 2001

(54) PATELLA REAMING SYSTEM

(76) Inventors: Brian D. Burkinshaw, 1014 Pecan Creek Dr.; Donald W. Dye, 803 Setting Sun Ct., both of Pflugerville, TX (US) 78660; Paul Salyer, 3208 N. 150 E., Warsaw, IN (US) 46580; Bryan Mendenhall, 4242 W. 525 S., Claypool, IN (US) 46510

( * ) Notice: Subject to any disclaimer, the term of this patent is extended or adjusted under 35 U.S.C. 154(b) by 0 days.

(21) Appl. No.: 09/150,125

(22) Filed: Sep. 9, 1998

(51) Int. Cl.[7] .................................................. A61B 17/00
(52) U.S. Cl. ............................................................... 606/80
(58) Field of Search ............................ 606/80, 81, 88, 606/87, 86, 96, 89, 205

(56) References Cited

U.S. PATENT DOCUMENTS

| | | | |
|---|---|---|---|
| 5,180,384 | 1/1993 | Mikhail | 606/80 |
| 5,222,955 | 6/1993 | Mikhail | 606/80 |
| 5,284,482 | 2/1994 | Mikhail | 606/86 |
| 5,520,692 | 5/1996 | Ferrante | 606/80 |
| 5,536,271 * | 7/1996 | Daly et al. | 606/80 |
| 5,542,947 | 8/1996 | Treacy | 606/88 |
| 5,575,793 * | 11/1996 | Carls et al. | 606/80 |
| 5,658,291 | 8/1997 | Techiera | 606/80 |
| 5,716,360 * | 2/1998 | Baldwin | 606/80 |
| 5,716,362 | 2/1998 | Treacy | 606/87 |

FOREIGN PATENT DOCUMENTS 08098842   4/1996   (JP) .

OTHER PUBLICATIONS

Zimmer, Inc.; Product Literature; Surgical Steps for Patella Sizing; pp. 30–34.
Smith and Nephew, Inc.; Product Literature; Surgical Steps for Patella Sizing; pp. 24–27.

* cited by examiner

*Primary Examiner*—Michael Buiz
*Assistant Examiner*—(Jackie) Tan-Uyen T. Ho

(57) ABSTRACT

An instrument for preparing a human patella for implanting a patellar prosthesis. A support member includes a quick-release base member mounted adjacent a first end of the support member. A reamer member is removably mounted on the quick-release base member. An attachment release member is resiliently mounted on the support member for movement into and out of engagement with the quick-release member and the reamer member. A stop member is adjustably mounted for limited movement on the support member to a plurality of calibrated positions for setting a controlled depth for movement of the reamer member.

30 Claims, 13 Drawing Sheets

PATELLA REAMING SYSTEM

BACKGROUND

The disclosures herein relate generally to a human patellar implant and more particularly to an apparatus and method of preparing a patella for implanting a patellar prothesis.

Preparation of a human patella for implanting a patellar prothesis is a multi-step process involving the removal of bone material and requires the use of several surgical tools. The need for such a prothesis is usually for correcting arthritic damage to the patella. Ideally, the same amount of bone removed from the patella is replaced by the prothesis so that the reconstructed patella will replicate the natural patella.

Generally, the surgical steps of such a procedure include preparation of the patella, reaming the patella, and securing the implant to the reamed patella. The reaming procedure is generally accomplished by securing the patella in a clamp and reaming a cylindrical bore in a portion of the patella to allow for insertion of an implant therein. The implant is then press-fit into the bore, or pressed into the bore and held in place by a clamp until a bonding agent cures to secure the implant in the patella.

Various tools and procedures have been developed to accomplish the above. U.S. Pat. No. 5,180,384 discloses a method for preparing a patella for receiving a patellar implant and for implanting a prothesis therein. An elongated passageway is formed in the patella which is then reamed to form a cavity of a size and configuration to receive the patellar prothesis using a cannulated reamer telescoped over a guide rod positioned in the elongated passageway.

In U.S. Pat. No. 5,284,482, a universal patellar clamp is disclosed. The clamp includes an articular surface clamping member having a central aperture defining a centerline axis. The central aperture is sized to accept all available known sizes of cannulated reamers. An anterior clamping member is positioned along the centerline axis and is movable with respect to the articular clamping member to effect clamping of the patella. A pair of guide arms are engaged with the articular clamping member to be positioned over the central aperture and provide a guide hole for supporting a threaded guidewire or pin along the centerline axis. The guide arms are removable from their position over the central aperture to clear the aperture for access by the cannulated reamer.

U.S. Pat. No. 5,520,692 discloses an adjustable depth patella recessing guide and method for guiding a cutting tool to recess the posterior surface of a patella. The guide includes a body having a first end for engaging the posterior surface of the patella, having a second end, and having a bore extending between the first and second ends for allowing the cutting tool to pass therethrough. A depth gauge is mounted within the bore of the body for movement in a direction between the first and second ends of the body. The depth gauge includes a stop for stopping the cutting tool. A lock mechanism is provided for locking the depth gauge to the body.

In U.S. Pat. 5,536,271, a system is disclosed for preparing a natural patella for implantation of a patellar prothesis. Substantially the same amount of bone removed from the natural patella is replaced by the prothesis so that the reconstructed patella will replicate the natural one in diameter and thickness. To this end, the patella is held stationary and two operations are performed simultaneously. First, a posterior side of the patella is resected to form a prothesis receiving surface for reception of a fixation surface of the patellar prothesis. Second, a mounting bore is formed into the resected surface of the patella for reception of fixation members of the patellar prothesis. A reamer is guided for movement between a first position spaced from the posterior surface of the patella, and a second position in operative engagement with the patella, at which formation of both the receiving surface and of the mounting bore therein has been completed. The reamer is stopped at the second position which is preselected according to the thickness of the patella, such that the amount of the patella removed is substantially equal to the thickness of the patellar prothesis.

U.S. Pat. No. 5,575,793 discloses an improved patella clamp apparatus including a scissor-like instrument fame having a pair of handles at one end portion. A patella holder and drill collet have gripping surfaces for holding a patient's patella therebetween during preparation for implantation of a prothesis. The collet has arcuate slots for accepting the vertical ridge of the patella. A reamer or cutting instrument cuts a circular recess into the posterior face of the patella. The collet is supported by the frame and positioned opposite the elevator. The collet accepts a depth stop for referencing the posterior aspect of the patella. The collet provides a bore that supports a reamer or drill for forming the circular recess in the patella posterior surface.

In U.S. Pat. No. 5,658,291, a median ridge referencing system and method of use in prosthetic knee implantation surgery is provided. The median ridge referencing system comprises a patella clamp including a guide sleeve having a length and a lumen extending through the length and referencing device comprising a stop ring and stop plug. The ring may be coupled to the guide sleeve at a plurality of locations along the length of the guide sleeve. The stop plug is removably coupled to the stop ring, and extends into the lumen of the guide sleeve until it reaches the bone. The stop ring is then coupled to the guide sleeve and the stop plug is removed. A reamer is inserted into the lumen of the guide sleeve and used to ream the patella until the reamer's stop reaches the top of the stop ring. When the reamer reaches the top of the stop ring, the patella has been reamed to the proper depth for insertion of the patella prosthesis.

In U.S. Pat. No. 5,716,360, a patella recession instrument and method provides a guide for producing an oval, tri-oval, or elliptically shaped recess on the posterior surface of the osteotomized patella for receiving a similarly shaped backing portion of a patellar implant. The apparatus includes a guide bushing and a bushing positioning mechanism for securing the bushing against the posterior of the osteotomized patella, with a guide opening formed through the bushing covering the total area to be recessed. A reamer guide structure, which may be a separate structure received in the bushing guide opening, or integrally formed with the bushing, receives one or more rotary reamer tools in a plurality of reaming positions. The cutting face of the rotary reamer tool in each different reaming position covers a different portion of the total area to be recessed. The recession method includes securing the guide bushing in the proper operating position against the patella, sequentially positioning the cutting face of the reamer tool or tools in the plurality of different reaming positions, and operating the tool or tools to produce a series of intermediate recesses that combine or approximate the total area to be recessed.

U.S. Pat. No. 5,716,362 discloses a patella milling instrument having a planar base with a fixed patellar clamping element formed thereon. A movable patellar milling element is slidably mounted on the base and is movable towards and away from the fixed clamping element. A drive element is operable between the base and the movable element for moving the movable clamping element. The drive element is actuated by a drive mechanism fixed in a handle of the device found at one end thereof and connected to a drive element which is also in the form of a ratchet element. A movable end mill type cutting element is mounted on a support arm supported by the base. The support arm is capable of movement in directions parallel to the plane of the base and is adjustable in a direction perpendicular to the base. The end mill has a drive shaft rotatably mounted in a bushing in an end of the support arm. The drive shaft is rotatable by a power tool and capable of movement in a direction perpendicular to the plane of the base.

Other attempts have been made to produce an efficient, easy-to-use patella reaming system for establishing the proper bore depth. However, these systems have commonly relied on the use of cumbersome spacers, commonly referred to as "donuts", to set the depth of penetration that a reamer makes when forming the bore for the insert. Still, other systems have used cumbersome external scales, calipers, threaded stop-nuts, fixed stops, or other devices to achieve this purpose. Each of these systems requires numerous, time consuming steps for making tool and attachment changes.

Therefore, what is needed is an apparatus and a method which permits the surgeon to predicably control reamer penetration depth, make one handed adjustments if needed, and made quick reamer size exchanges during the procedure.

SUMMARY

One embodiment, accordingly, uses an integral scale and simple push-button release that allows the surgeon to easily gage the depth of penetration of a reamer from the point of contact wit the articular surface of the patella, and to make one-handed adjustments as needed. To this end, a patella reaming apparatus includes a support member having a quick-release base member mounted thereon. An attachment release member is resiliently mounted on the support member for movement in and out of engagement with the guide-release base member. A stop member is adjustably mounted on the support member for movement to a plurality of calibrated positions.

A principal advantage of this embodiment is that penetration depth is predictable and repeatable. Reamer exchange to different sizes are also simple to accomplish with a quick-release mechanism located on the barrel of the reamer body. A built-in adjustable depth setting is provided with a stop collar.

BRIEF DESCRIPTION OF THE DRAWING FIGURES

DETAILED DESCRIPTION

Figure 1:
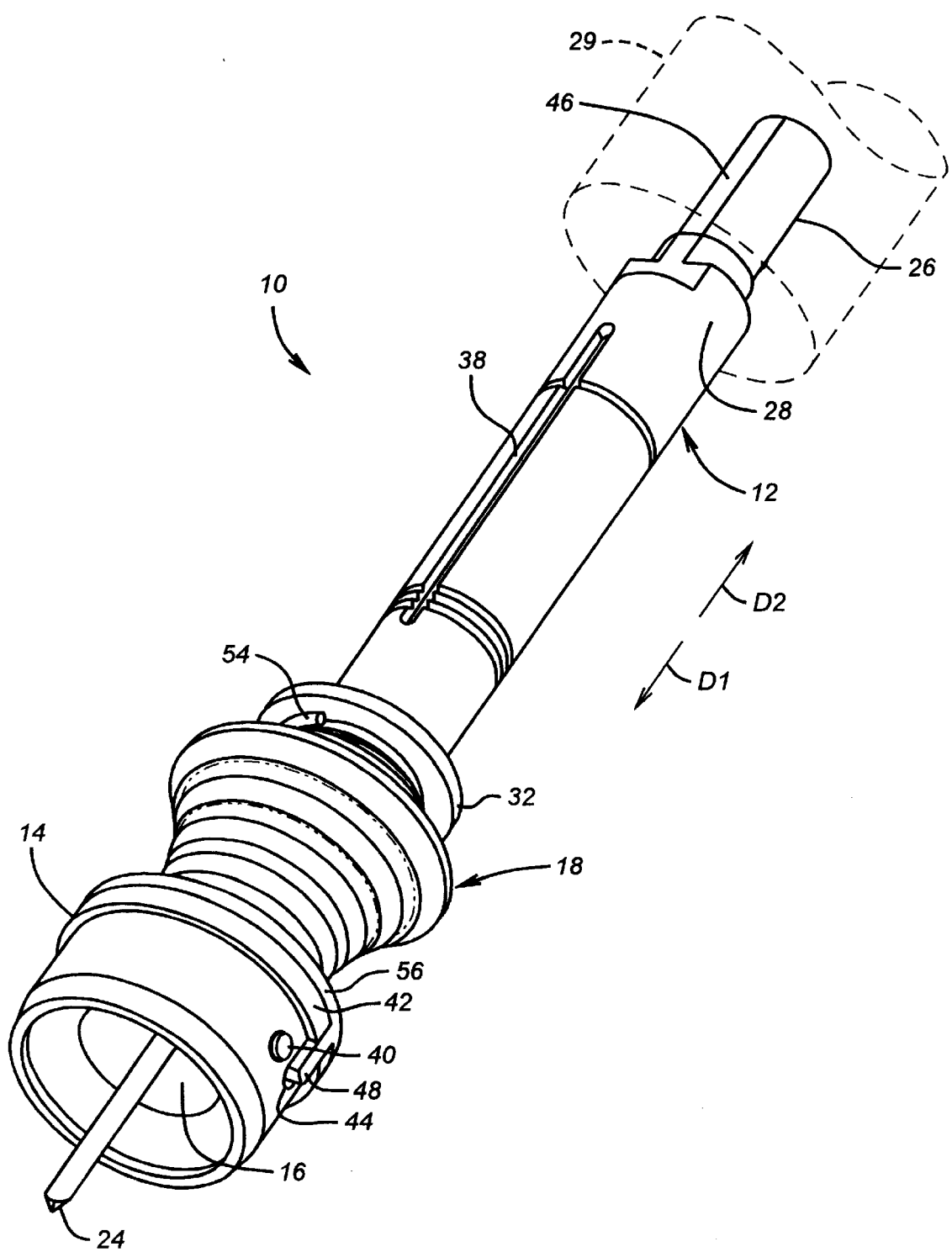
FIG. 1 is perspective view illustrating an embodiment of a portion of a patella reaming apparatus.

A patella reaming apparatus is generally designated 10 in FIG. 1 and includes a support member 12, a quick-release base member 14, mounted adjacent a first end 16 of support member 12, and attachment release member 18, resiliently mounted on the support member 12 for movement into and out of engagement with the quick-release base member 14. In addition, a stop member 20, FIG. 2, is adjustably mounted on the support member 12, for movement to a plurality of calibrated positions, and a reamer member 22 is removably mounted on quick-release base member 14. A drill tip 24, FIGS. 1 and 2, is mounted at the first end 16 of the support member 12, and extends from the quick-release base member 14. A power tool receiving head 26, FIG. 1, is mounted on a second end 28 of the support member 12 to enable reaming apparatus 10 to be rotatably driven by attachment of a power tool 29.

Figure 2:
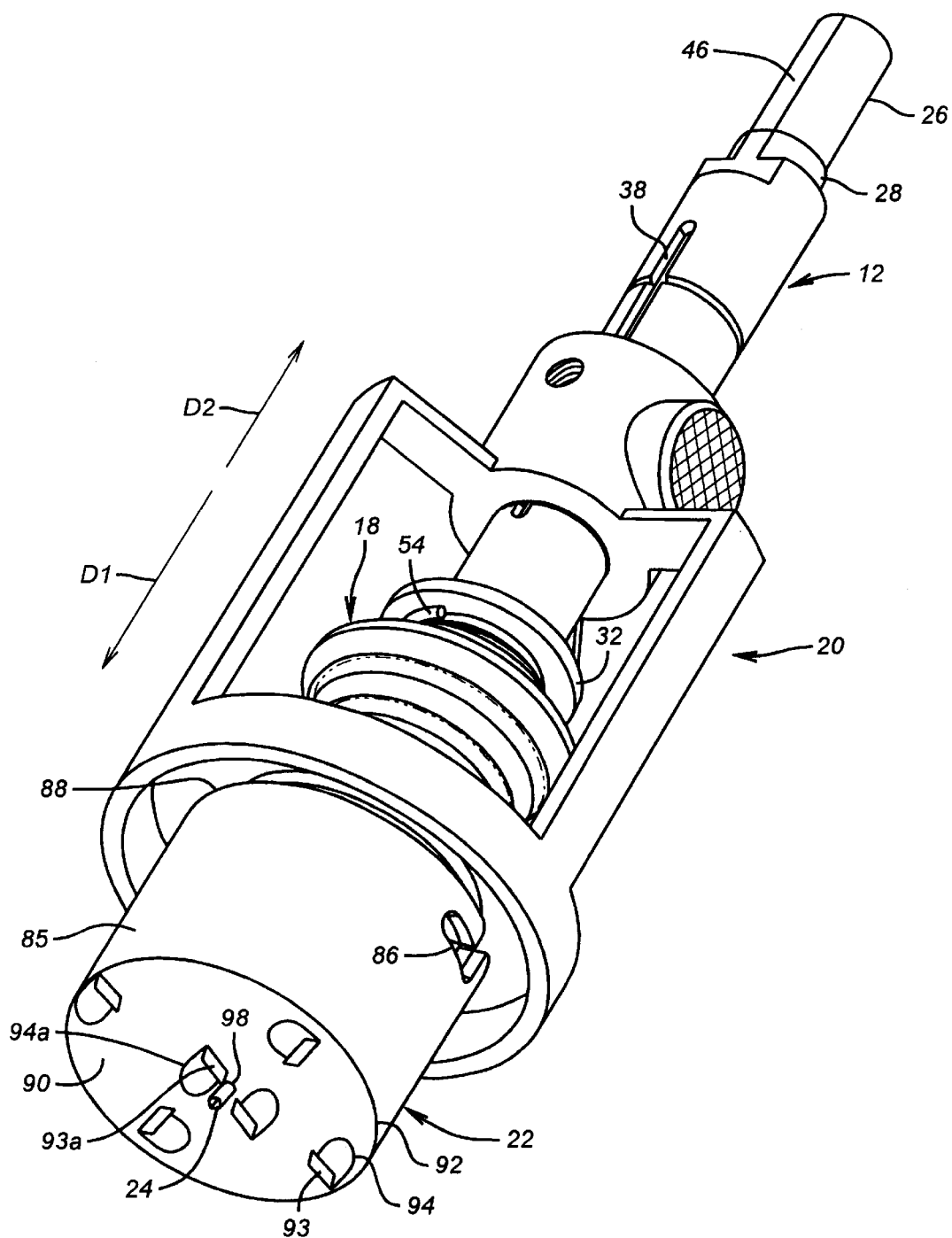
FIG. 2 is a perspective view illustrating another embodiment of the patella reaming apparatus.
Figures 3, 4:
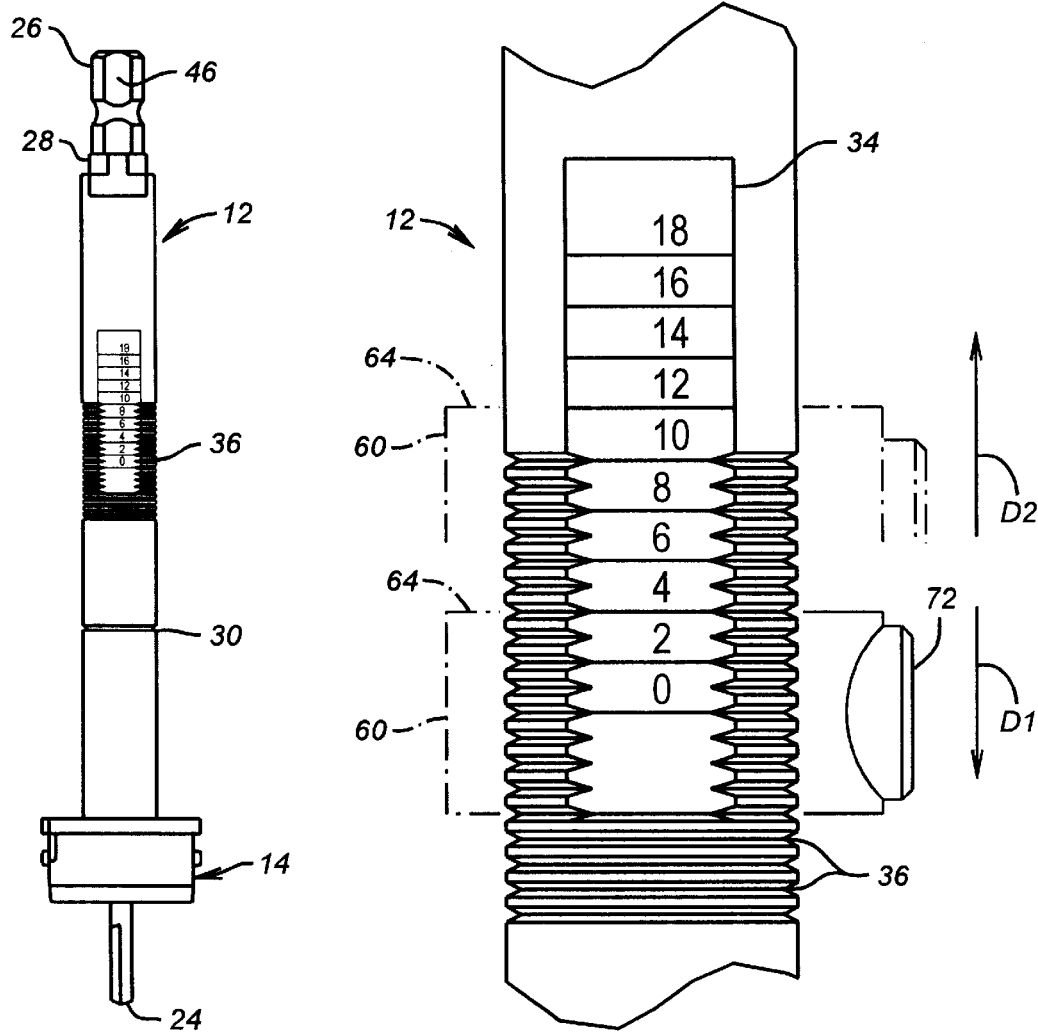
FIG. 3 is a side view illustrating an embodiment of a support member of the reaming apparatus.
FIG. 4 is a partial view illustrating an embodiment of a calibrated scale on the support member.
Figure 5:
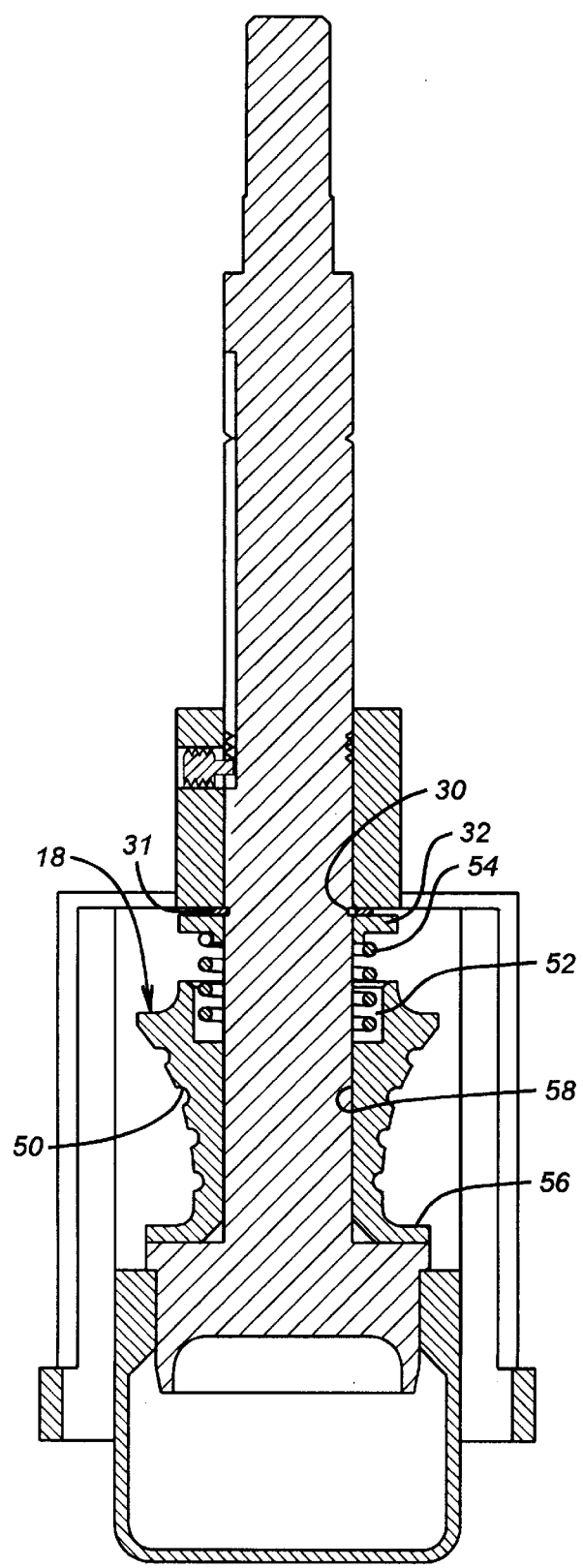
FIG. 5 is a cross-sectional side view taken along the line 5—5 of FIG. 7

Support member 12, FIG. 3, is an elongated shaft including an annular groove 30 formed therein for receiving a snap ring 31 to limit movement of a stationary ring 32, FIG. 5, secured therein. In addition, support member 12 includes a calibrated scale 34, FIGS. 3 and 4, and a plurality of annular notches 36 formed therein adjacent the scale 34. An elongated groove 38, FIGS. 1 and 2 is provided in support member 12. A plurality of flats 46, FIGS. 1–3 are formed on power tool receiving head 26 at second end 28 of support member 12.

Figure 1A:
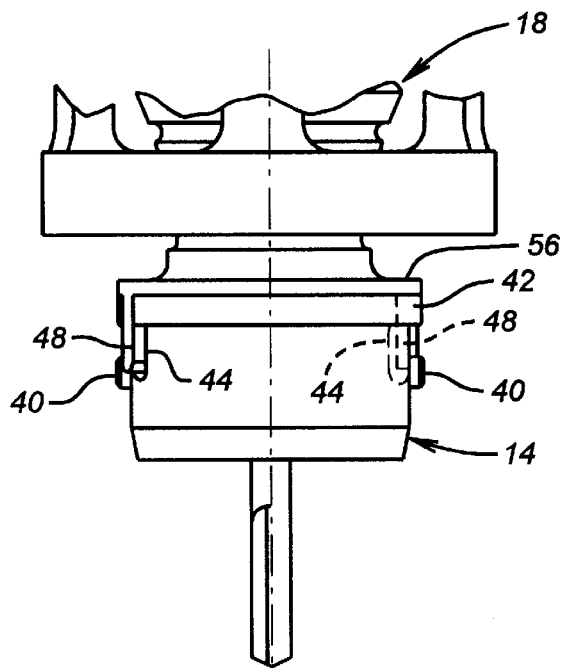
FIG. 1A is a partial side view illustrating an embodiment of a first end of a support member of the reaming apparatus.

The quick-release base member 14 is annular and includes a pair of opposed protrusions 40 extending transversely therefrom, see also FIG. 1A. An annular flange 42 is formed on base member 14 and a pair of opposed grooves 44 are formed to extend axially into base member 14 through annular flange 42 and terminate adjacent the protrusion 40.

Figure 6:
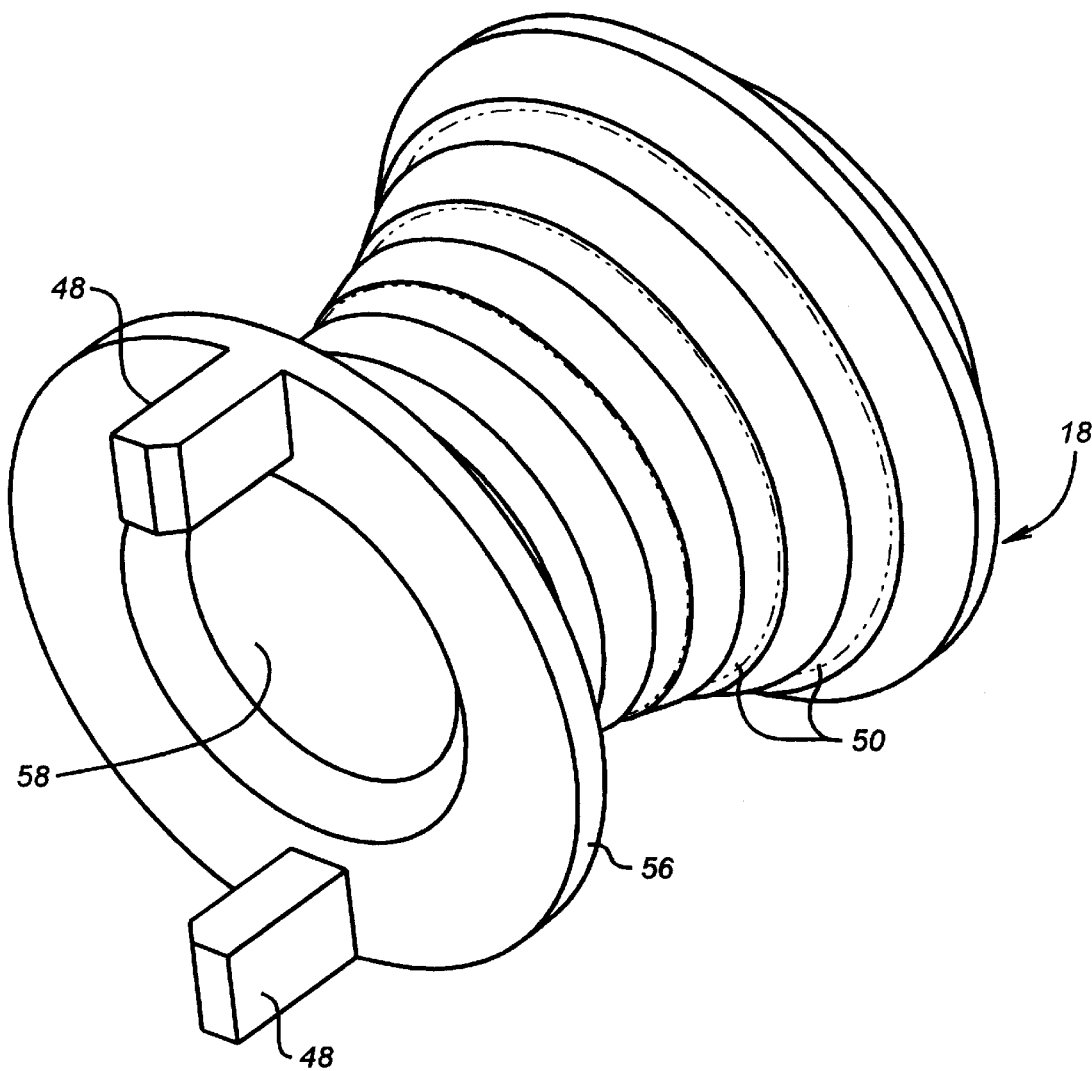
FIG. 6 is an enlarged perspective view illustrating an embodiment of an attachment release member of the reaming apparatus.
Figure 7:
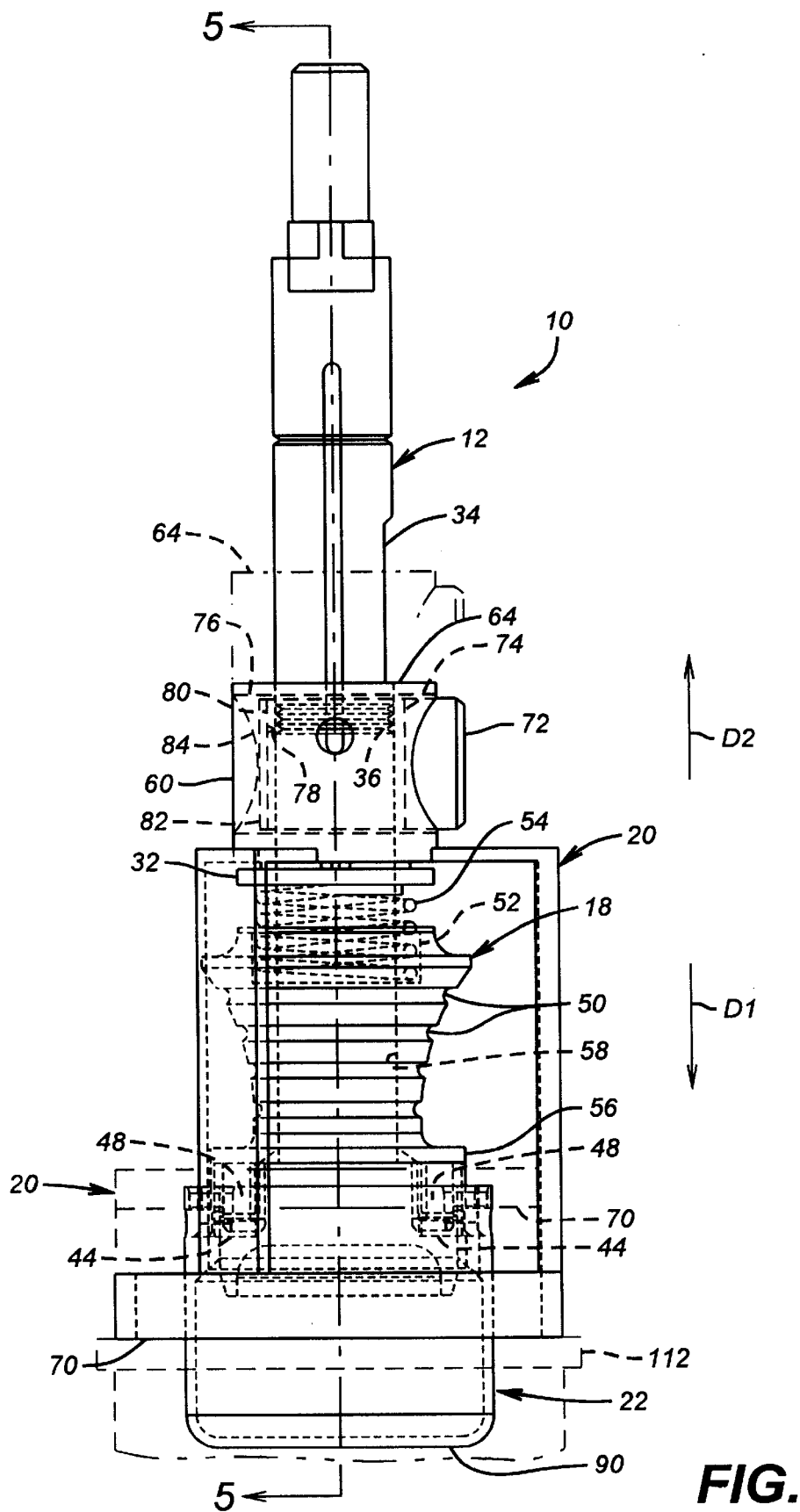
FIG. 7 is a side view illustrating an embodiment of the reaming apparatus.

Attachment release member 18, FIGS. 5–7 is tapered and is provided with a plurality of annular grooves 50 to improve manual gripping. An annular recess 52 in attachment release member 18 is provided to receive a resilient member such as a coil spring 54 retained in compression on support member 12, between recess 52 and stationary ring 32. A flange 56, see also FIGS. 1 and 1A, formed on attachment release member 18, includes a pair of tabs 48, which extend therefrom. Tabs 48 are urged by spring 54 in a direction D1 into grooves 44 of the quick-release base member 14. A bore 58 formed in attachment release member 18, receives support member 12.

Figure 8:
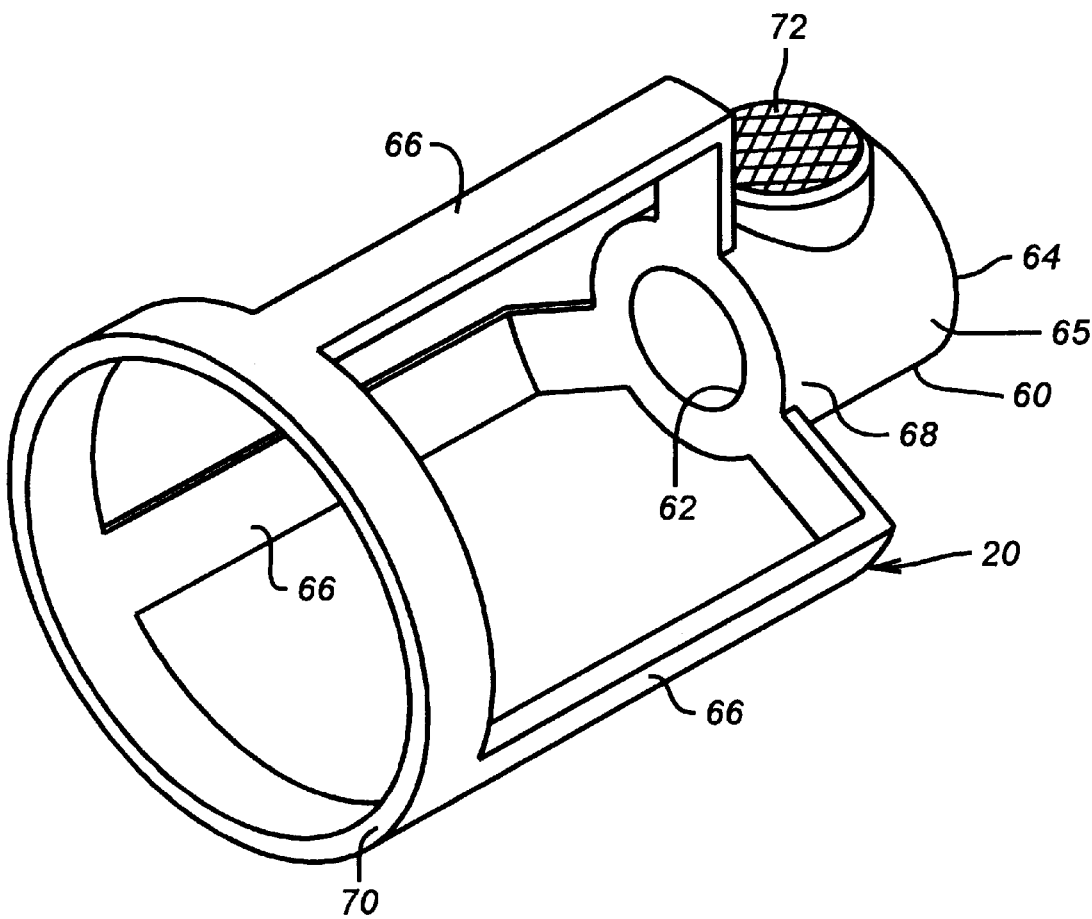
FIG. 8 is a perspective view illustrating an embodiment of a stop member of the reaming apparatus.

Stop member 20, FIG. 8, includes an annulus 60 including a bore 62 formed therein for receiving support member 12. A reference surface 64 is at a first end 65 of annulus 60. A plurality of support legs 66 extend outwardly and downwardly from a second end 68 of annulus 60 and terminate at an annular stop surface 70. A release 72 is resiliently mounted in annulus 60 for releasable engagement with support member 12. Release 72, FIG. 7, includes an oversized throughbore 74 for receiving support member 12. Release 72 is resiliently mounted in a bore 76 formed in annulus 60. A tooth 78 formed in a wall 80 protrudes into throughbore 74. An end surface 82 of release 72 engages a resilient washer member 84 which urges tooth 78 into any one of the adjacent notches 36. When release 72 is manually urged toward washer 84, the washer 84 is compressed as tooth 78 is disengaged from its respective notch 36. As such, stop member 20 may be set at adjusted positions along the length of support member 12. Thus, reference surface 64 may be adjustably mounted on support member 12 to a plurality of calibrated positions along scale 34, see also FIG. 4.

Figure 2A:
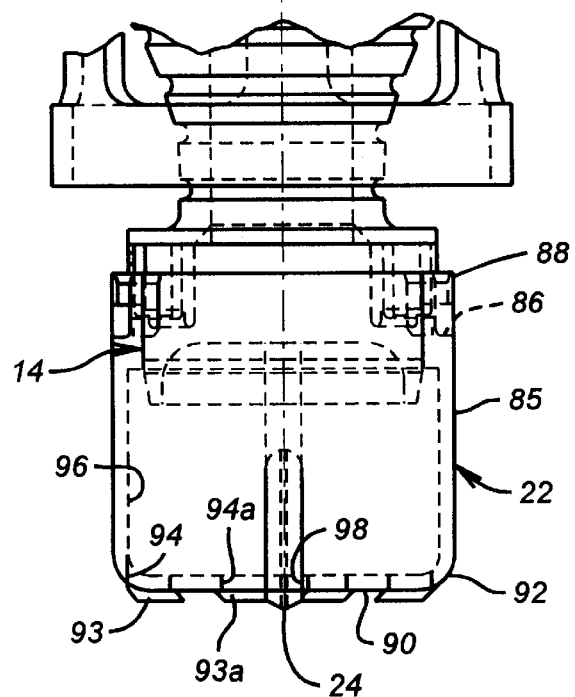
FIG. 2A is a partial side view illustrating an embodiment of a reamer member attached to a quick-release base member.

Reamer member 22, FIGS. 2 and 2A, is generally cup-shaped having a cylindrical sidewall 85 which includes a pair of L-shaped grooves 86 formed therein adjacent a first end 88 thereof, and a reaming face 90 adjacent a second end 92 thereof. Reaming face 90 includes a plurality of reamer blades 93 raised from face 90, and a scoop 94 adjacent each blade 93. In this manner, bone material reamed by a blade 93 is directed into the respective adjacent scoop 94 and captured in an interior cavity 96 of reamer member 22. In addition, a central aperture 98 which is continuous with its most adjacent blade 93a and scoop 94a permits drill tip 24 to extend beyond reaming face 90. This feature advantageously clears the center of a reamed surface of any irregularities which may be missed due to non-rotation of the blades 93 at the center of face 90. As a result, a planar surface is reamed which permits full contact seating of an insert pressed into a bore prepared by reamer member 22, as is discussed below in greater detail.

Figure 9:
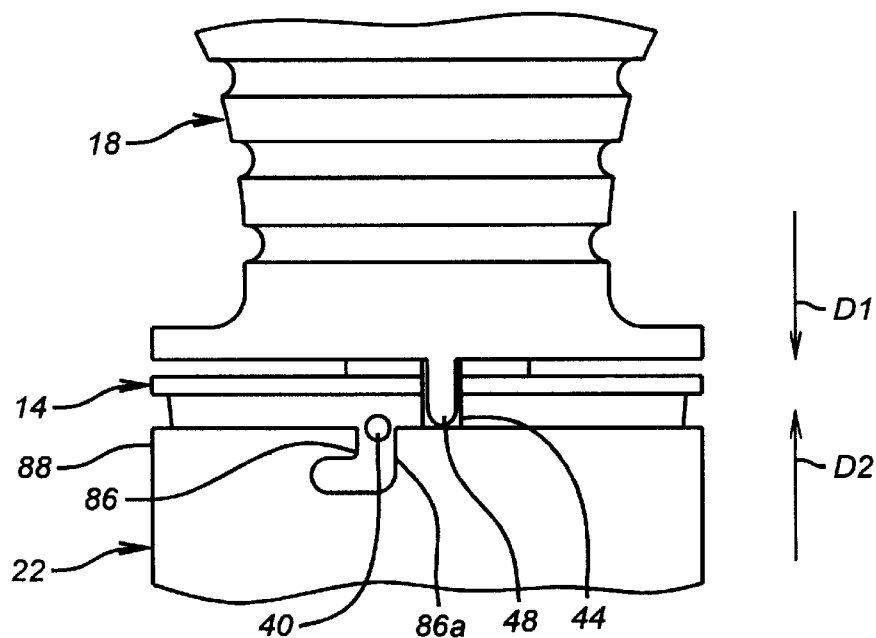
FIGS. 9–9D are partial view illustrating embodiments of attachment and removal of the reamer member.
Figure 9A:
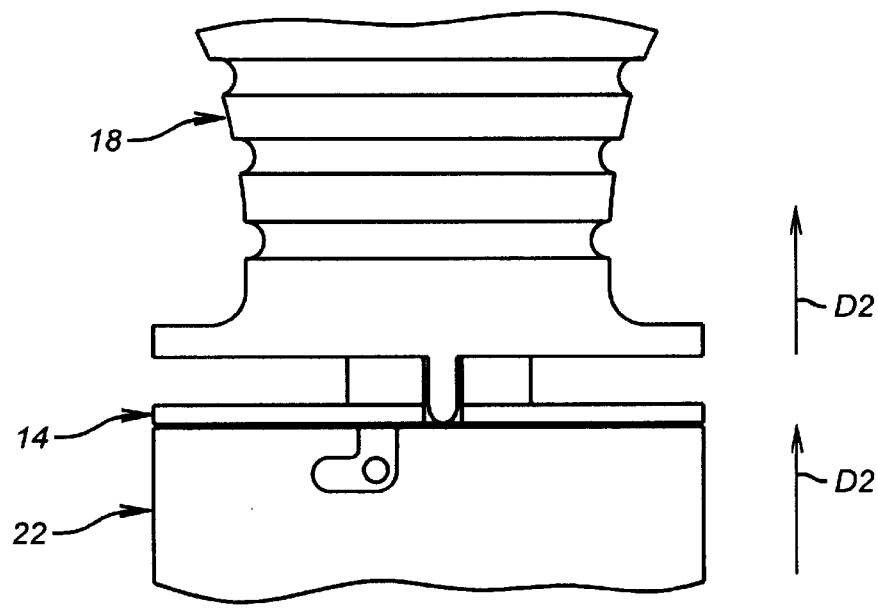
Figure 9B:
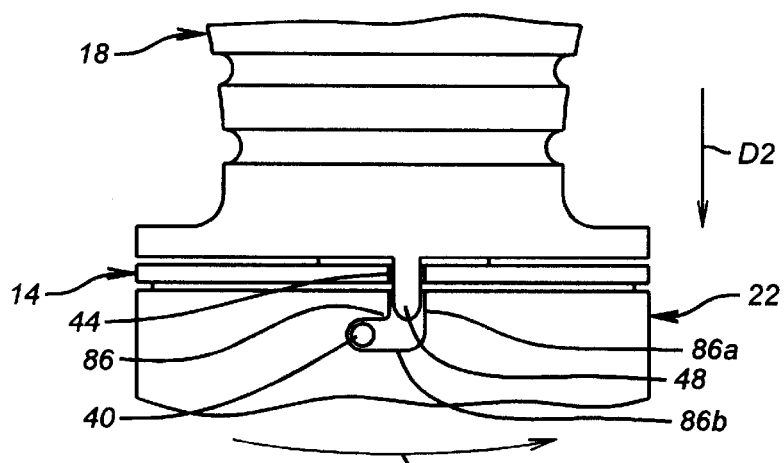

Attachment and removal of reamer member 22 on quick-release base member 14 is easily and quickly accomplished. Attachment release member 18 is urged in an axial direction D1 by coil spring 54, FIG. 7, such that tabs 48, are urged into slot 44 of quick release base member 14, see also FIG. 9. Reamer member 22, is engaged with quick-release base member 14 and moved in an axial direction D2 until first end 88 engages tabs 48 (only one of which is shown) and protrusion 40 is aligned with a first portion 86a of slot 86. Further movement of reamer member 22 in direction D2, FIG. 9A, urges attachment release member 18 away from quick-release base member 14. Rotation of reamer member 22 in a rotational direction R1, FIG. 9B, positions protrusion 40 in a second portion 86b of slot 86 and permits the above-mentioned coil spring (not shown in FIG. 9B) to urge tabs 48 in direction D1 into first portion 86a of slot 86. This captures reamer member 22 from either axial or rotational movement relative to quick-release base member 14.

Figure 9C:
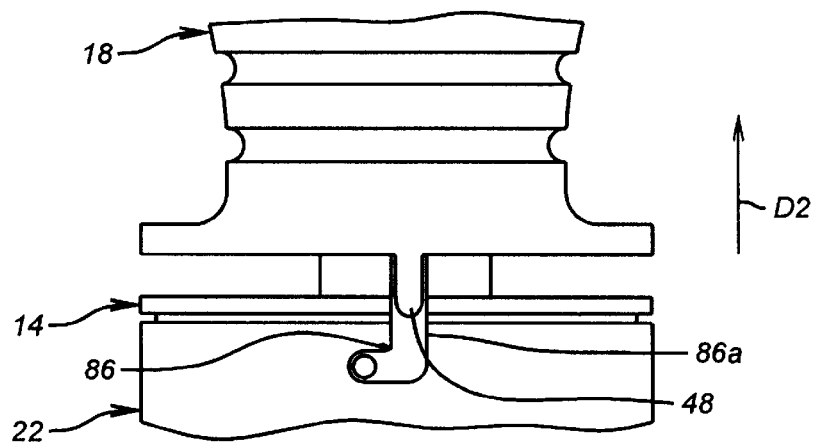
Figure 9D:
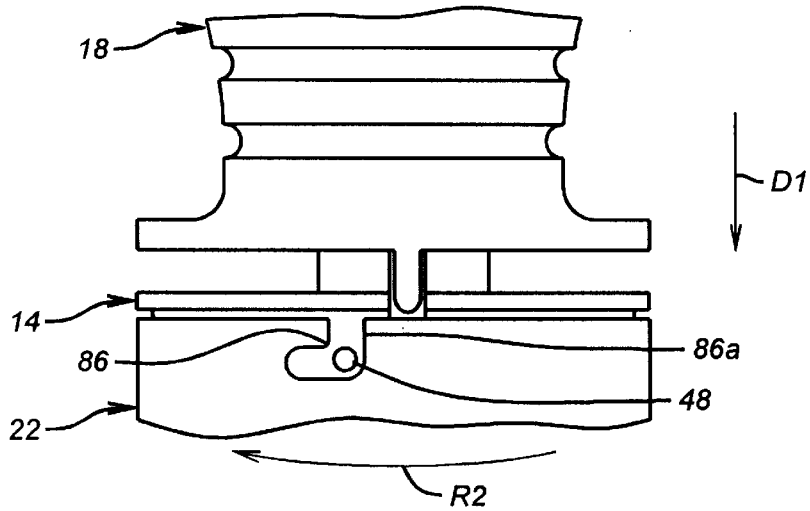

Removal of reamer member 22, FIG. 9C, is accomplished by moving attachment release member 18 away from quick-release base member 14 in axial direction D2 so as to withdraw tabs 48 from first portion 86a of slot 86. This permits rotation of reamer member 22, FIG. 9D, in a rotational direction R2, to position protrusion 40 in alignment with first portion 86a of slot 86, thus enabling reamer member 22 to be disengaged from quick-release base member 14 in axial direction D1.

Figure 10:
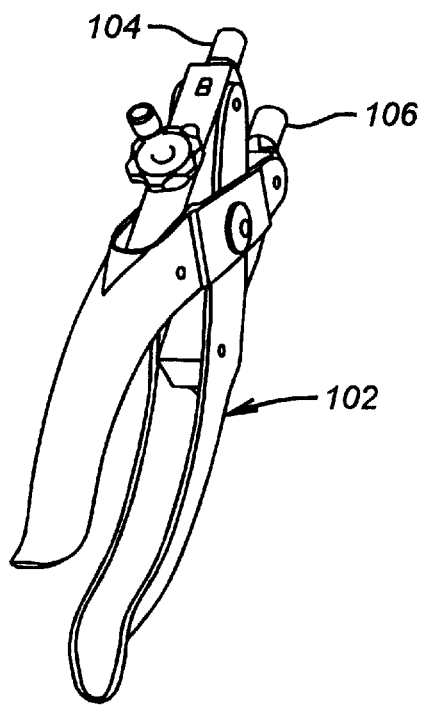
FIG. 10 is a perspective view illustrating an embodiment of a clamp used with the reaming apparatus.
Figure 11:
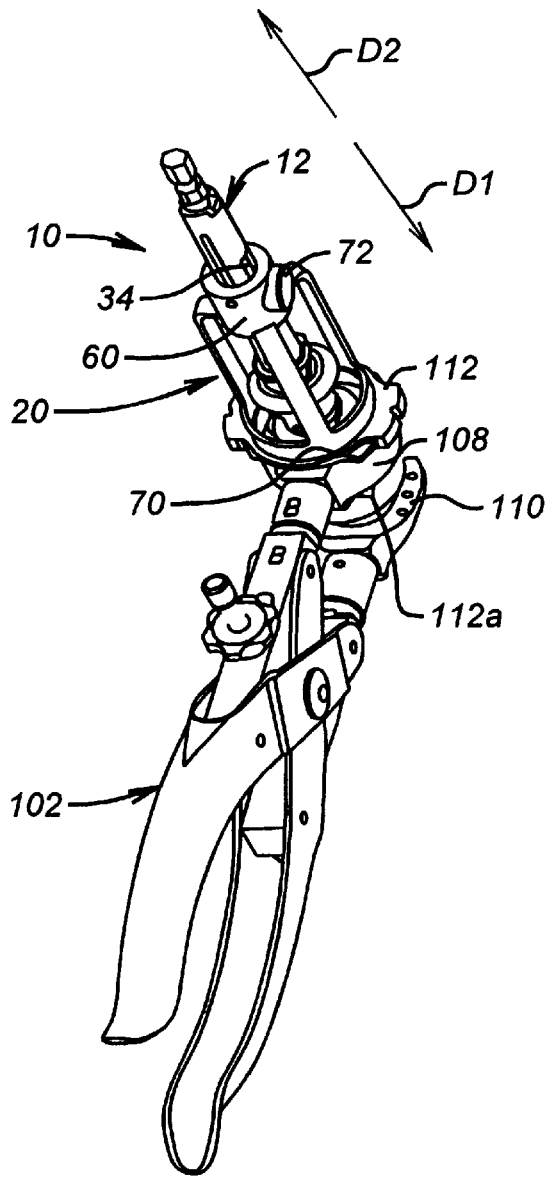
FIG. 11 is a perspective view illustrating an embodiment of the reaming apparatus mounted in the clamp.

A known adjustable clamp 102, FIG. 10, includes a first attachment member 104 and a second attachment member 106 provided for attachment to a known ring member 108, FIG. 11, and a known fork member 110. A known bushing 112 is seated in ring member 108 and cam-locked therein. Clamp 102 can then be used to grip a patella, not shown in FIG. 11, between a grip end 112a of the bushing 112, and fork member 110. Reamer apparatus 10, FIGS. 7 and 11 is seated in bushing 112 such that reamer face 90 engages the patella. By depressing release 72, stop member 20 is released to move relative to support member 12, in direction D1, thus permitting stop surface 70 to engage bushing 112. At this point, a first reading is made as illustrated by way of example in FIG. 4, on calibrated scale 34, by alignment of reference surface 64 therewith, to establish a first reference point. Release 72, is again released permitting stop member 20 to be moved in direction D2, relative to support member 12, to another alignment of reference surface 64 on calibrated scale 34, to establish a second reference point. This spaces stop surface 70 from bushing 112, FIG. 7. The difference between the first and second reference points represents a predetermined reaming depth, or depth of penetration of reamer member 22 into the patella, based on the thickness of the patella and the thickness of the implant to be inserted into the patella. By attaching a power tool 29, FIG. 1, to the tool receiving head 26 of support member 12, reamer member 22, FIG. 7, is rotated into the patella in direction D1 until stop surface 70 engages bushing 112, which limits further movement of the reamer member 22.

Figure 12:
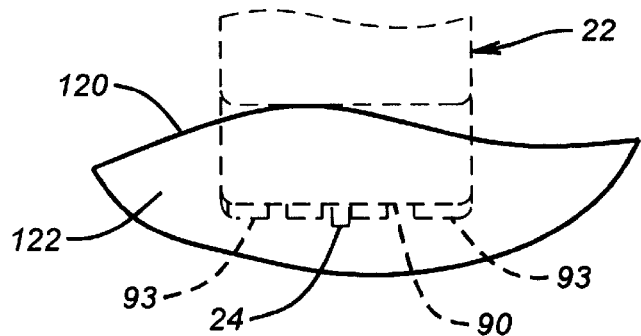
FIG. 12 is a diagrammatic side view illustrating an embodiment of a reamer member forming a bore in a human patella.
Figure 13:
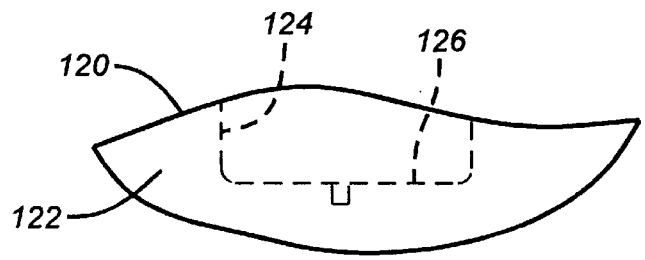
FIG. 13 is a diagrammatic side view illustrating an embodiment of the patella having the bore formed therein.
Figure 16:
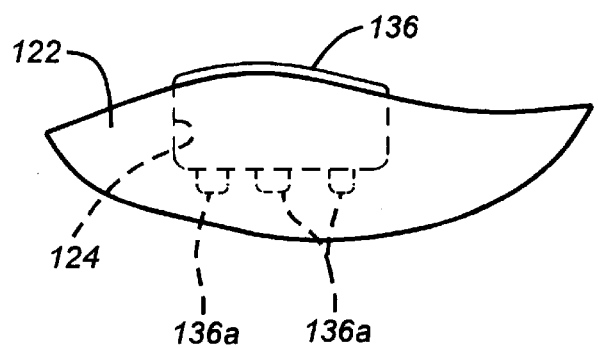
FIG. 16 is a diagrammatic side view illustrating an embodiment of the bore in the patella including an implant therein.
Figure 14:
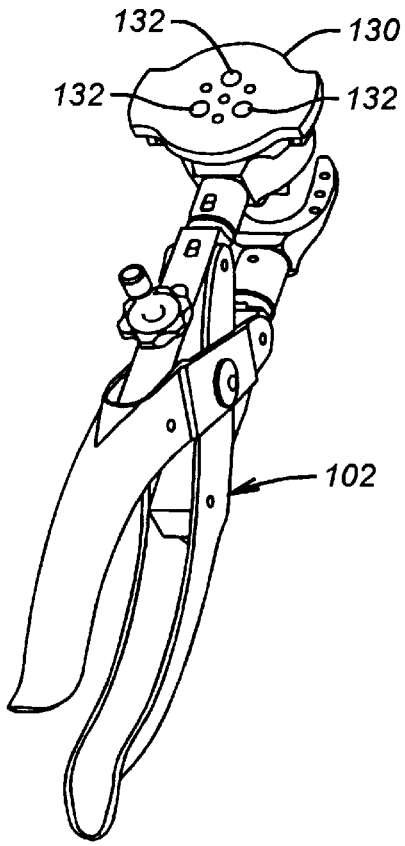
FIG. 14 is a perspective view illustrating an embodiment of a drill guide mounted on the clamp.
Figure 14A:
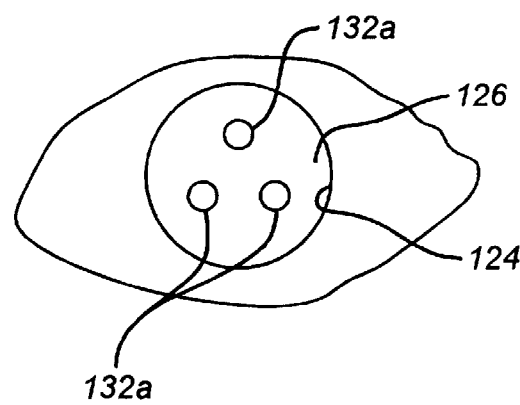
FIG. 14a is a diagrammatic top view illustrating an embodiment of the bore in the patella including peg holes formed therein.
Figure 15:
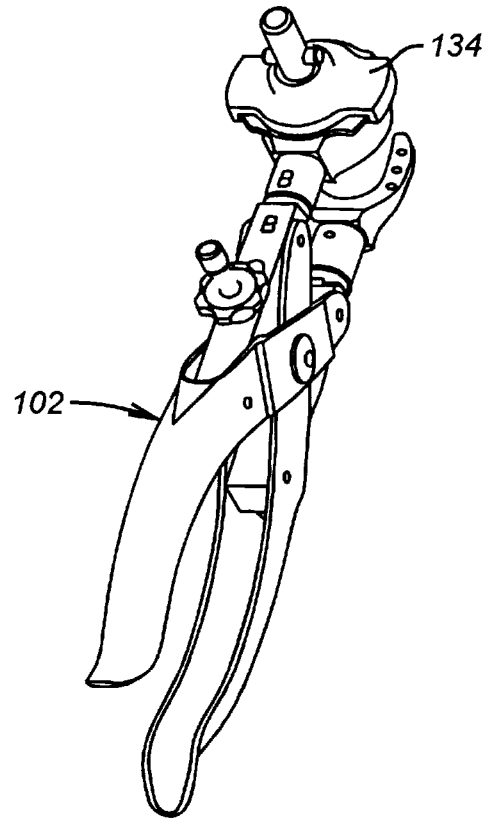
FIG. 15 is a perspective view illustrating an embodiment of a press mounted on the clamp.

FIG. 12 illustrates reamer member 22 engaged with a surface 120 of a patella 122. Reamer face 90 rotates into patella 122, forming a bore 124, see also FIG. 13. Drill tip 24 and blades 93, remove irregularities from surface 126, of bore 124, to ensure proper seating of an insert therein. A drill guide member 130, FIG. 14 is attached to clamp 102 via a cam-lock to utilize drill holes 132 to form a plurality of implant fixation peg holes 132a in surface 126 of bore 124, FIG. 14a. Drill guide 130 may be oriented as illustrated or rotated 180°, whichever is preferred, to position the maximum number of pegs in the best quality of bone in patella 122. A press member 134, FIG. 15 may replace drill guide 130 and attach to clamp 102 via a cam lock for press fitting an insert 136, FIG. 16, into bore 124. Insert 136, including a plurality of pegs 136a may be either press-fit into bore 124 or may be cemented with a bonding agent as is well known. Insert 136 is intended to replace the same or slightly more bone material than that removed from patella 122.

In operation, the present embodiments provide an integral calibrated scale and easily accessible manual push button release which allows a surgeon to easily control the depth of penetration of the reamer from the point of contact with the articular surface of the patella. One-handed adjustments are easily made. Penetration depth is predictable and repeatable. Reamer exchanges to different sizes are quick and easy to accomplish with a one-handed quick-release device located on the main support member of the reamer apparatus.

As a result, one embodiment provides a patella reaming apparatus including a support member having a quick-release base member mounted adjacent a first end of the support member. An attachment release member is resiliently mounted on the support member for movement into and out of engagement with the quick-release base member. A stop member is adjustably mounted on the support member for movement to a plurality of calibrated positions.

Another embodiment provides an instrument for preparing a human patella for implanting a patellar prothesis including a support having a quick-release base member mounted adjacent a first end of the support member, and a reamer member removably mounted on the quick-release base member. An attachment release member is resiliently mounted on the support member for movement into and out of engagement with the quick-release base member and the reamer member. A stop member is adjustably mounted for limited movement on the support member to a plurality of calibrated positions for setting a controlled depth for movement of the reamer member.

Another embodiment provides a quick-release patella reaming apparatus including a support member having a quick-release base member mounted adjacent a first end of the support member, and an attachment release member resiliently mounted on the support member for movement into and out of engagement with the quick-release base member. A stop member is adjustably mounted for limited movement on the support member to a plurality of calibrated positions between the first end and a second end of the support member. A drill tip is mounted at the first end of the support member and extends from the quick-release base member. A power tool receiving head is mounted on the second end of the support member.

Still another embodiment provides a patella reaming system including an adjustable clamp having a ring member and a fork member attached in opposed positions to the clamp. A bushing is mounted on the ring. A support member, including a quick-release base member having a reamer removably mounted thereon, is inserted into the bushing. An attachment release member is resiliently mounted on the support member for movement into and out of engagement with the quick release base member and the reamer. A stop member is adjustably mounted for limited movement on the support member to a plurality of calibrated positions for setting a controlled depth for movement of the reamer.

A further embodiment provides a method of preparing a human patella for implanting a patellar prothesis. A ring attachment and a fork attachment are attached in opposed positions on an adjustable clamp. A bushing is mounted in a locked position in the ring attachment. The human patella is clamped between the bushing attachment and the ring attachment. A reamer is attached to a quick-release base member mounted on a first end of a support member. The reamer is inserted into the bushing to a position wherein a face of the reamer engages the patella. A stop member, which is adjustably mounted on the support member, is positioned in engagement with the bushing. A calibrated scale on the support member is read to establish a first reference point. The stop member is adjusted on the support member, to a second reference point along the calibrated scale spaced from the bushing. The difference between the first and second reference points determines a depth of penetration of the reamer into the patella. A power driver is attached to a second end of the support member for rotating the reamer into the patella to the penetration depth, determined by the stop member engaging the bushing, to remove bone material from the patella and form a bore for receiving the patellar prosthesis.

As it can be seen, the principal advantages of these embodiments are that penetration depth is predictable and repeatable due to the built-in adjustable depth setting provided with a stop collar. Reamer exchanges to different sizes are simple to accomplish by using a quick, one-handed release for exchanging reamer cutter bodies. The release is easy to clean. The clamp used for securing the patella, does not need to be removed until preparation of the patella is complete.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed:

1. A patella reaming apparatus comprising:
   a support member;
   a quick-release base member mounted adjacent a first end of the support member;
   an attachment release member, resiliently mounted on the support member for movement into and out of engagement with the quick-release base member; and
   a stop member formed from one piece and adjustably mounted on the support member for movement to a plurality of calibrated positions, wherein the stop member is shaped as a cage extending around the support member and having at least one leg extending from a first end to a second end, and the stop member has a release member at the first end to engage the support member and a stop surface at the second end.

2. The apparatus a defined in claim 1 wherein the the stop member includes at least two legs that extend from the first end to the second end.

3. The apparatus as defined in claim 1 wherein the cage forms at least one opening adapted to provide access to the support member.

4. The apparatus as defined in claim 1 wherein the stop member includes three legs that are parallel with the support member and extend from the first end to the second end.

5. The apparatus as defined in claim 4 wherein the first end is configured as an annulus and includes the release member.

6. The apparatus as defined in claim 4 wherein the support member includes a stationary ring mounted thereon.

7. The apparatus as defined in claim 6 wherein the attachment release member is mounted between the stationary ring and the quick-release base member.

8. The apparatus as defined in claim 7 wherein a resilient member is mounted between the stationary ring and the attachment release member.

9. The apparatus as defined in claim 8 wherein the attachment release member includes a tab extending therefrom, the resilient member urging the attachment release member toward the quick-release base member so that the tab extends into the groove.

10. The apparatus as defined in claim 1 wherein the support member includes a calibrated scale, and a plurality of notches formed thereon.

11. The apparatus as defined in claim 10 wherein the stop member includes a resiliently mounted release connected thereto for releasable engagement with the notches for moving the stop member along the calibrated scale.

12. The apparatus as defined in claim 11 wherein the stop member includes an annulus having a reference surface adjacent the calibrated scale.

13. The apparatus as defined in claim 12 wherein the stop member includes a stop surface.

14. The apparatus as defined in claim 5 wherein the support member includes a power tool receiving head mounted on a second end thereof, opposite the first end.

15. An instrument for preparing a human patella for implanting a patellar prothesis comprising:
   a support member;
   a quick-release base member mounted adjacent a first end of the support member;
   a reamer member, removably mounted on the quick-release base member;
   an attachment release member resiliently mounted on the support member for movement into and out of engagement with the quick-release base member and the reamer member; and
   a one-piece stop member adjustably mounted for limited movement on the support member to a plurality of calibrated positions for setting a controlled depth for movement of the reamer member, wherein the stop member extends around the support member from a first end having a release member to engage the support member and to a second end having a stop surface and has at least one leg extending from the first end to the second end.

16. The instrument as defined in claim 15 wherein the quick-release base member is fixedly mounted on the support member and the stop member is shaped as cage having three legs that extend from the first end to the second end.

17. The instrument as defined in claim 16 wherein the reamer member includes a slot formed therein and the stop member has a cylindrical configuration.

18. The instrument as defined in claim 17 wherein the quick-release base member includes a projection for engaging the slot in the reamer member.

19. The instrument as defined in claim 18 wherein the attachment release member includes a tab extending therefrom for engagement with the slot in the reamer member.

20. The instrument as defined in claim 19 wherein the attachment release member secures the reamer member on the quick-release base member in response to the projection being positioned in the slot and the tab being resiliently urged into the slot.

21. The instrument as defined in claim 20 wherein the attachment release member permits release of the reamer member from the quick-release base member in response to the attachment release member being moved to withdraw the tab from the slot.

22. The instrument as defined in claim 15 further comprising a drill tip mounted at the first end and extending through an opening formed in a face of the reamer member.

23. The instrument as defined in claim 15 wherein the support member includes a calibrated scale, and plurality of notches formed therein.

24. The instrument as defined in claim 23 wherein the stop member includes a resiliently mounted release connected thereto for releasable engagement with the notches, for moving the stop member along the calibrated scale.

25. The instrument as defined in claim 24 wherein the stop member includes an annulus having a reference surface adjacent the calibrated scale.

26. The instrument as defined in claim 25 wherein the stop member includes a stop surface.

27. The instrument as defined in claim 22 wherein the support member includes a power tool receiving head mounted on a second end thereof, opposite the first end.

28. A quick-release patella reaming apparatus comprising:
   a support member;
   a quick-release base member mounted adjacent a first end of the support member;
   an attachment release member resiliently mounted on the support member for movement into and out of engagement with the quick-release base member;
   a one-piece stop member adjustably mounted for limited movement on the support member to a plurality of calibrated positions between the first end and a second end of the support member, the stop member being shaped as a cage extending around the support member and having at least one leg connected to the first and second ends and having a first end with a release member to engage the support member and a second end with a stop surface;
   a drill tip mounted at the fist end of the support member and extending from the quick-release base member; and
   a power tool receiving head mounted on the second end of the support member.

29. A patella reaming system comprising:
   an adjustable clamp;
   a ring member and fork member attached in opposed positions on the adjustable clamp;
   a bushing mounted on the ring member;
   a support member, including a quick-release base member having a reamer removably mounted thereon, the reamer being inserted into the bushing;
   an attachment release member resiliently mounted on the support member for movement into and out of engagement with the quick-release base member and the reamer; and
   a one-piece stop member adjustably mounted for limited movement on the support member to a plurality of calibrated positions for setting a controlled depth for movement of the reamer, the stop member extends around the support member from a first end having a release member to engage the support member and to a second end having a stop surface and has at least one leg connected to the first and second ends.

30. A method of preparing a human patella for implanting a patellar prosthesis comprising the steps of:
   attaching a ring attachment and a fork attachment in opposed position on an adjustable clamp;
   mounting a bushing in a locked position on the ring attachment;
   clamping the human patella between the bushing and the fork attachment;
   attaching a reamer to a quick-release base member mounted on a first end of a support member;
   inserting the reamer into the bushing to a position wherein a face of the reamer engages the patella;
   positioning a stop member, adjustably mounted on the support member, to a position engaging the bushing, wherein the stop member is one-piece and extends around the support member and has a first end having a release member to engage the support member and to a second end having a stop surface and has at least one leg extending from the first end to the second end;

reading a calibrated scale on the support member to establish a first reference point;

adjusting the stop member on the support member, to a second reference point along the calibrated scale spaced from the bushing, the difference between the first and second reference points determining a penetration depth of the reamer into the patella; and attaching a power driver to a second end of the support member for rotating the reamer into the patella to the penetration depth, determined by the stop member engaging the bushing, to remove bone material from the patella and form a bore in the patella for receiving the patellar prosthesis.

* * * * *